US012770376B2

(12) United States Patent
Krogue et al.

(10) Patent No.: US 12,770,376 B2
(45) Date of Patent: Oct. 20, 2026

(54) MAXIMIZING GENERALIZABLE PERFORMANCE BY EXTRACTION OF DEEP LEARNED FEATURES WHILE CONTROLLING FOR KNOWN VARIABLES

(71) Applicant: Google LLC, Mountain View, CA (US)

(72) Inventors: Justin David Krogue, San Francisco, CA (US); Po-Hsuan Chen, Palo Alto, CA (US); Yun Liu, Mountain View, CA (US); Ellery Alyosha Wulczyn, Oakland, CA (US); David Francis Steiner, Redwood City, CA (US)

(73) Assignee: GOOGLE LLC, Mountain View, CA (US)

( * ) Notice: Subject to any disclaimer, the term of this patent is extended or adjusted under 35 U.S.C. 154(b) by 205 days.

(21) Appl. No.: 18/845,384

(22) PCT Filed: Mar. 9, 2023

(86) PCT No.: PCT/US2023/014916
§ 371 (c)(1),
(2) Date: Sep. 9, 2024

(87) PCT Pub. No.: WO2023/172692
PCT Pub. Date: Sep. 14, 2023

(65) Prior Publication Data

US 2025/0191344 A1 Jun. 12, 2025

Related U.S. Application Data

(60) Provisional application No. 63/318,028, filed on Mar. 9, 2022.

(51) Int. Cl.
*G06V 10/774* (2022.01)
*G06V 10/762* (2022.01)
(Continued)

(52) U.S. Cl.
CPC .......... *G06V 10/774* (2022.01); *G06V 10/762* (2022.01); *G06V 10/766* (2022.01);
(Continued)

(58) Field of Classification Search
CPC . G06T 7/11; G06T 2207/10104; G16H 30/40; A61B 6/5235; A61B 6/037; A61B 6/5205
See application file for complete search history.

(56) References Cited

U.S. PATENT DOCUMENTS 11,200,454 B1 * 12/2021 Qian .................... G06V 10/776
11,604,943 B2 * 3/2023 Tsai .................. G06F 18/21322
(Continued)

OTHER PUBLICATIONS

Akishima-Fukasawa et al., "Histopathological Predictors of Regional Lymph Node Metastasis at the Invasive Front in Early Colorectal Cancer", Histopathology, vol. 59, No. 3, Sep. 2011, pp. 470-481.
(Continued)

*Primary Examiner* — Mia M Thomas
(74) *Attorney, Agent, or Firm* — DORITY & MANNING, P.A.

(57) ABSTRACT

Provided are systems and methods for the generation of machine-learning features by clustering deep learning embeddings and selecting embedding cluster data while controlling for known associations. In particular, a computing system can use a pre-trained machine learning model (e.g., an image embedding model) to obtain embeddings of input images. The computing system can train a clustering algorithm (e.g., a k-means algorithm) to cluster these embeddings into one of a number (e.g., k) clusters. The computing system can then perform a selection process to select one or more (e.g., the top n) clusters that boost performance in a prediction model (e.g., a logistic regression model) trained with a combination of the selected clusters and one or more baseline features. In such fashion, the computer system can enable an improved combination of
(Continued)

extracted deep learned features and baseline features. This can maximize generalizable performance while controlling for known variables.

20 Claims, 6 Drawing Sheets

(51) Int. Cl.
*G06V 10/766* (2022.01)
*G06V 10/776* (2022.01)
*G06V 20/69* (2022.01)
*G16H 30/40* (2018.01)
*G16H 50/20* (2018.01)

(52) U.S. Cl.
CPC .......... *G06V 10/776* (2022.01); *G06V 20/698* (2022.01); *G16H 30/40* (2018.01); *G16H 50/20* (2018.01); *G06V 2201/03* (2022.01)

(56) References Cited

U.S. PATENT DOCUMENTS

| | | | | |
|---|---|---|---|---|
| 11,687,841 | B2 * | 6/2023 | Hagen | G06F 18/2433 382/159 |
| 11,769,582 | B2 * | 9/2023 | Tizhoosh | G16H 15/00 705/2 |
| 12,020,477 | B2 * | 6/2024 | Tizhoosh | G06F 16/532 |
| 2018/0053042 | A1 * | 2/2018 | Philbin | G06F 18/214 |
| 2019/0080164 | A1 * | 3/2019 | Duke | G06F 18/214 |
| 2020/0082212 | A1 * | 3/2020 | Alcock | G06F 16/56 |
| 2020/0163641 | A1 * | 5/2020 | Amit | A61B 6/12 |
| 2020/0387755 | A1 * | 12/2020 | Hagen | G06F 18/2155 |
| 2021/0366577 | A1 * | 11/2021 | Koller | G16B 40/20 |
| 2022/0027758 | A1 * | 1/2022 | Kreshpa | G06N 3/0442 |
| 2022/0245800 | A1 * | 8/2022 | Champagne | G06V 10/774 |
| 2022/0375576 | A1 * | 11/2022 | Liao | G16H 30/40 |
| 2022/0384042 | A1 * | 12/2022 | Sellergren | A61B 6/50 |
| 2023/0350880 | A1 * | 11/2023 | Shreve | G06F 16/2379 |
| 2024/0119593 | A1 * | 4/2024 | Marie-Nelly | G06T 7/0012 |
| 2024/0333578 | A1 * | 10/2024 | Mehta | G06N 7/01 |
| 2025/0061690 | A1 * | 2/2025 | Liao | G06F 21/6218 |
| 2025/0117893 | A1 * | 4/2025 | Steiner | G06T 5/60 |
| 2025/0324948 | A1 * | 10/2025 | Pandey | G06V 40/10 |
| 2026/0051063 | A1 * | 2/2026 | Aravamudan | G06T 7/0016 |

OTHER PUBLICATIONS

Altman et al., “Prognosis and Prognostic Research: Validating a Prognostic Model”, BMJ, vol. 338, No. 7709, Jun. 20, 2009, pp. 1487-1490.
Brinker et al., “Deep Learning Approach to Predict Sentinel Lymph Node Status Directly from Routine History of Primary Melanoma Tumours”, European Journal of Cancer, vol. 154, Sep. 2021, pp. 227-234.
Brockmoeller et al., “Deep Learning Identifies Inflamed Fat as a Risk Factor for Lymph Node Metastasis in Early Colorectal Cancer”, The Journal of Pathology, vol. 256, No. 3, Mar. 2022, pp. 269-281.
Bychkov et al., “Deep Learning Based Tissue Analysis Predicts Outcome in Colorectal Cancer”, Scientific Reports, vol. 8, No. 3395, Feb. 21, 2018, 11 pages.
Chen et al., “A Simple Framework for Contrastive Learning of Visual Representations”, Proceedings of the Thirty-Seventh International Conference on Machine Learning, Vienna, Austria, Jun. 12-18, 2020, 11 pages.
Compton et al., “The Staging of Colorectal Cancer: 2004 and Beyond”, Ca: A Cancer Journal for Clinicians, vol. 54, Issue 6, Nov./Dec. 2004, pp. 295-308.
Courtiol et al., “Deep Learning-Based Classification of Mesothelioma Improves Prediction of Patient Outcome”, Nature Medicine, vol. 25, No. 10, Oct. 7, 2019, 18 pages.
De Burlet et al., “Total Number of Lymph Nodes in Oncologic Resections, Is There More to Be Found?”, Journal of Gastrointestinal Surgery, vol. 19, No. 5, Feb. 18, 2015, pp. 943-948.
He et al., “Deep Residual Learning for Image Recognition” 2016 Institute of Electrical and Electronics Engineers Conference on Computer Vision and Pattern Recognition, Las Vegas, Nevada, United States, Jun. 27-30, 2016, 9 pages.
Hedge et al., “Similar Image Search for Histopathology: Smily”, NPJ Digital Medicine, vol. 2, No. 56, Jun. 21, 2019, 9 pages.
Huppertz et al., “Biobank Graz: The Hub for Innovative Biomedical Research”, The Hub for Innovative Biomedical Research, vol. 3, Jul. 22, 2016, 6 pages.
International Search Report and Written Opinion for PCT/US2023/0141916, mailed on Jun. 23, 2023, 16 pages.
Juan et al., “Graph-Rise: Graph-Regularized Image Semantic Embedding”, arXiv: 1902.108814v1, Feb. 14, 2019, 9 pages.
Kiehl et al., “Deep Learning can Predict Lymph Node Status Directly from Histology in Colorectal Cancer”, European Journal of Cancer, vol. 157, Nov. 2021, pp. 464-473.
Kolesnikov et a., “Big Transfer (BiT): General Visual Representation Learning”, ECCV 2020: Sixteenth European Conference, Glasgow, United Kingdom, Aug. 23-28, 2020, 17 pages.
Krouge et al., “Predicting Lymph Node Metastasis from Primary Tumor Histology and Clinicopathologic Factors in Colorectal Cancer using Deep Learning”, Communications Medicine, vol. 3, No. 59, Apr. 24, 2023, 9 pages.
Kwak et al., “Deep Convolutional Neural Network-Based Lymph Node Metastasis Prediction for Colon Cancer Using Histopathological Images”, Frontiers in Oncology, vol. 10, Jan. 13, 2021, 9 pages.
Marley et al., “Epidemiology of Colorectal Cancer”, International Journal of Molecular Epidemiology and Genetics, vol. 7, No. 3, Sep. 2016, pp. 105-114.
Mobadersany et al., “Predicting Cancer Outcomes from Histology and Geonomics using Convolutional Networks”, Proceedings of the National Academy of Sciences, vol. 115, No. 13, Mar. 12, 2018, pp. 2970-2979.
Moons et al., “Risk Prediction Models: II. External Validation, Model Updating, and Impact Assessment”, Heart, vol. 98, No. 9, Mar. 2012, 9 pages.
Moons et al., “Transparent Reporting of a Multivariable Prediction Model for Individual Prognosis or Diagnosis (Tripod): Explanation and Elaboration”, vol. 162, No. 1, Jan. 6, 2015, 73 pages.
Ong et al., “Assessment of Lymph Node Involvement in Colorectal Cancer”, World Journal of Gastrointestinal Surgery, vol. 8, Issue 3, Mar. 27, 2016, pp. 179-192.
Rahbari et al., “Molecular Detection of Tumor Cells in Regional Lymph Nodes is Associated with Disease Recurrence and Poor Survival in Node-Negative Colorectal Cancer: A Systematic Review and Meta-Analysis”, Journal of Clinical Oncology, vol. 30, No. 1, Nov. 28, 2011, 14 pages.
Russakovsky et al., “ImageNet Large Scale Visual Recognition Challenge”, arXiv: 1409.0575v3, Jan. 30, 2015, 43 pages.
Schmitt et al., “Hidden Variables in Deep Learning Digital Pathology and Their Potential to Cause Batch Effects: Prediction Model Study”, Journal of Medical Internet Research, vol. 23, No. 2, Feb. 2, 2021, 8 pages.
Skrede et al., “Deep Learning for Prediction of Colorectal Cancer Outcome: A Discovery and Validation Study”, Lancet, vol. 395, Issue 10221, Feb. 1, 2020, pp. 350-360.
Tlusty et al., “Unsupervised Clustering of Mammograms for Outlier Detection and Breast Density Estimation”, Twenty-Fourth International Conference on Pattern Recognition, Beijing, China, Aug. 20-24, 2018, pp. 3808-3813.
Verrill et al., “Histopathological Assessment of Lymph Nodes in Colorectal Carcinoma: Does Triple Levelling Detect Significantly More Metastases?”, Journal of Clinical Pathology, vol. 57, No. 11, Nov. 2004, pp. 1165-1167.
Vogel et al., “The American Society of Colon and Rectal Surgeons Clinical Practice Guidelines for the Management of Color Cancer”, Diseases of the Colon and Rectum, vol. 60, Oct. 2017, pp. 999-1017.

(56) References Cited

OTHER PUBLICATIONS

Wang et al., "Removing Confounding Factors Associated Weights in Deep Neural Networks Improves the Prediction Accuracy for Healthcare Applications", Pacific Symposium on Biocomputing, vol. 24, 2019, 17 pages.
Wulczyn et al., "Interpretable Survival Prediction for Colorectal Cancer using Deep Learning", Nature Partner Journals Digital Medicine, vol. 4, No. 71, Apr. 19, 2021, 13 pages.
Yamauchi et al., "Pathological Predictors for Lymph Node Metastasis in TI Colorectal Cancer", Surgery Today, vol. 38, No. 10, 2008, pp. 905-910.
Zech et al., "Confounding Variables can Degrade Generalization Performance of Radiological Deep Learning Models", arXiv: 1807.00431v2, Jul. 13, 2018, 15 pages.

* cited by examiner

MAXIMIZING GENERALIZABLE PERFORMANCE BY EXTRACTION OF DEEP LEARNED FEATURES WHILE CONTROLLING FOR KNOWN VARIABLES

RELATED APPLICATIONS

This application is a national stage filing under 35 U.S.C. § 371 of PCT Application Number PCT/US2023/014916, filed Mar. 9, 2023, which claims priority to and the benefit of U.S. Provisional Patent Application No. 63/318,028, filed Mar. 9, 2022. Each of PCT Application Number PCT/US2023/014916 and U.S. Provisional Patent Application No. 63/318,028 is hereby incorporated by reference in its entirety.

FIELD

The present disclosure relates generally to machine learning. More particularly, the present disclosure relates to systems and methods for the generation of machine-learning features by clustering deep learning embeddings and selecting embedding cluster data while controlling for known associations.

BACKGROUND

Machine learning-based models can include various types of models (e.g., neural networks or other multi-layer models, logistic regression models, linear models, etc.) that learn associations between inputs and outputs. Specifically, the values of the parameters of a machine learning model can be iteratively learned so that the model produces a desired output (e.g., classification) when given feature data for a particular input instance or "case". One example task that a machine learning model can perform is a diagnostic task in which the model predicts a medical diagnosis for a particular case when provided with input information (e.g., feature data) for a case. As an example, the input data for a case can include imagery such as histological imagery, radiological imagery, natural imagery, etc.

Various types of features exist that can be provided as inputs to a machine learning model. Some features may be basic (e.g., not-learned) features that describe known or previously determined characteristics of a particular case. In some examples, these basic features may be provided by a human or determined via a manual or simple process such as looking up raw feature data from a file or table. One example baseline feature of this type might include information such as the location or age of a user.

Another type of features are "deep" features or other "learned" features that are themselves produced by a machine learning model. One example feature of this type can include embeddings (e.g., numerical vectors expressed within a learned dimensional space) produced by an embedding model. Typically, these embeddings are very information rich—that is, they contain significant and complex inter-related information about an input case. Embeddings can often contain or be expressed using a large number (e.g., 64, 300, etc.) of dimensions.

One basic approach for training a machine learning model is to simply provide the model with only the learned features (e.g., embeddings) as input. However, without controlling for features with known association to the output (e.g., baseline features), a deep learning model may simply learn these same, known associations. Therefore, such a machine learning model may not exhibit any improvement in performance relative to a model trained on the baseline features alone, or may not exhibit any improvement in performance when later supplied with the baseline features in addition to the learned features.

Another approach for training a model using both baseline and learned features (e.g., embeddings) is to simply provide both of these feature types as input to the model together (e.g., by concatenating the embedding with the baseline features and then providing the concatenated data as input). However, in this approach, the richness, depth, and/or complexity of the embedding feature data may overwhelm the baseline feature data and the resulting model may not exhibit any improvement in performance relative to a model trained on the learned features alone. Likewise, the full embedding feature data may simply capture the same associations provided by the baseline features.

SUMMARY

Aspects and advantages of embodiments of the present disclosure will be set forth in part in the following description, or can be learned from the description, or can be learned through practice of the embodiments.

One example aspect of the present disclosure is directed to computer-implemented method to generate machine-learning features, the method comprising: obtaining, by a computing system comprising one or more computing devices, a plurality of training cases, wherein each training case has a plurality of training images associated therewith; processing, by the computing system, the plurality of images associated with each of the plurality of training cases with a machine-learned image embedding model to generate a plurality of image embeddings respectively for the plurality of images; assigning, by the computing system, each image embedding to one of a number of embedding clusters; generating, by the computing system, a respective cluster quantitation vector for each training case that indicates an amount of the image embeddings associated with such training case that were assigned to each of the number of embedding clusters; evaluating, by the computing system, a respective change in performance of a machine-learned prediction model when respectively supplied with the cluster quantitation vector values for each embedding cluster in addition to a set of one or more baseline features; and selecting, by the computing system, one or more embedding clusters of the number of embedding clusters for use as machine-learning features based at least in part on the respective changes in performance of the machine-learned prediction model associated with the embedding clusters.

In some implementations, the plurality of training images associated with each training case comprise patches sampled from a larger image.

In some implementations, the method further comprises, prior to assigning, by the computing system, each image embedding to one of the number of embedding clusters: processing, by the computing system, an initial set of images with the machine-learned image embedding model to generate an initial set of image embeddings; and performing, by the computing system, a clustering algorithm on the initial set of image embeddings to establish the number of embedding clusters having cluster centroids. In some implementations, wherein the clustering algorithm comprises a k-means clustering algorithm.

In some implementations, evaluating, by the computing system, the respective change in performance of the machine-learned prediction model when respectively supplied with the cluster quantitation vector values for each embedding cluster in addition to the set of one or more baseline features comprises evaluating, by the computing system, the respective change in an area under the curve performance metric for the machine-learned prediction model when respectively supplied with the cluster quantitation vector values for each embedding cluster in addition to the set of one or more baseline features.

In some implementations, selecting, by the computing system, the one or more embedding clusters for use as machine-learning features comprises iteratively selecting, by the computing system, two or more of the embedding clusters in a greedy stepwise fashion.

In some implementations, the machine-learned image embedding model comprises a pre-trained image embedding model that has been previously trained on out-of-distribution imagery. In some implementations, the machine-learned image embedding model comprises a pre-trained image embedding model that has been previously trained on in-distribution imagery.

In some implementations, the machine-learned prediction model comprises a logistic regression model.

In some implementations, the machine-learned prediction model comprises a diagnostic model that generates a predicted medical diagnosis.

In some implementations, for each training case, the medical diagnosis comprises a predicted probability of a presence of a cancerous cell within the plurality of images associated with the training case. Example cancers include bladder cancer; breast cancer; cervical cancer; colorectal cancer; gynecologic cancers; head and neck cancers; kidney cancer; liver cancer; and others.

In some implementations, the plurality of images comprise a plurality of histological images. For example, the histological images can be histological images of tissue sampled from an area of interest (e.g., bladder tissue; breast tissue; cervical tissue; colorectal tissue; gynecologic tissue; head and neck tissue; kidney tissue; liver tissue; and others.).

In some implementations, the number of embedding clusters and a number of the one or more for use as machine-learning features comprise hyperparameters; and the method comprises performing a hyperparameter tuning process to determine values for the number of embedding clusters and the number of the one or more for use as machine-learning features.

In some implementations, the method further includes receiving, by the computing system, an inference case comprising a plurality of inference images; processing, by the computing system, the plurality of inference images with the machine-learned image embedding model to generate a plurality of inference embeddings respectively for the plurality of inference images; assigning, by the computing system, each inference embedding to one of the number of embedding clusters; generating, by the computing system, an inference cluster quantitation vector for the inference case that indicates an amount of the inference embeddings that were assigned to each of the number of embedding clusters; extracting, by the computing system, cluster quantitation vector values of the inference cluster quantitation vector that correspond to the selected embedding clusters; and processing, by the computing system, the extracted cluster quantitation vector values of the inference cluster quantitation vector and one or more baseline feature values associated with the inference case with the machine-learned prediction model to generate a prediction for the inference case.

Another example aspect is directed to a computer system, comprising: one or more processors; and one or more non-transitory computer-readable media that store instructions that, when executed by the one or more processors, cause the computer system to perform operations. The operations include: receiving, by the computing system, an inference case comprising a plurality of inference images; processing, by the computing system, the plurality of inference images with a machine-learned image embedding model to generate a plurality of inference embeddings respectively for the plurality of inference images; assigning, by the computing system, each inference embedding to one of a number of pre-defined embedding clusters; generating, by the computing system, an inference cluster quantitation vector for the inference case that indicates an amount of the inference embeddings that were assigned to each of the number of pre-defined embedding clusters; extracting, by the computing system, cluster quantitation vector values of the inference cluster quantitation vector that correspond to one or more selected embedding clusters, the one or more selected embedding clusters having been selected based on respective changes in performance of a machine-learned prediction model when respectively supplied with cluster quantitation vector values for each embedding cluster in addition to a set of one or more baseline features; and processing, by the computing system, the extracted cluster quantitation vector values of the inference cluster quantitation vector and one or more baseline feature values associated with the inference case with the machine-learned prediction model to generate a prediction for the inference case.

In some implementations, the plurality of inference images associated with the inference case comprise patches sampled from a larger inference image.

In some implementations, the machine-learned image embedding model comprises a pre-trained image embedding model.

In some implementations, the machine-learned prediction model comprises a logistic regression model.

In some implementations, the machine-learned prediction model comprises a diagnostic model that generates a predicted medical diagnosis for the inference case.

In some implementations, the medical diagnosis comprises a predicted probability of a presence of a cancerous cell within the plurality of inference images associated with the inference case.

Another example aspect is directed to a machine-learned prediction model or a non-transitory computer-readable medium storing a machine-learned prediction model that has been trained using cluster data associated with one or more selected embedding clusters, the one or more selected embedding clusters having been selected by the performance of operations. The operations comprising: obtaining, by a computing system comprising one or more computing devices, a plurality of training cases, wherein each training case has a plurality of training images associated therewith; processing, by the computing system, the plurality of images associated with each of the plurality of training cases with a machine-learned image embedding model to generate a plurality of image embeddings respectively for the plurality of images; assigning, by the computing system, each image embedding to one of a number of embedding clusters; generating, by the computing system, a respective cluster quantitation vector for each training case that indicates an amount of the image embeddings associated with such training case that were assigned to each of the number of embedding clusters; evaluating, by the computing system, a respective change in performance of a machine-learned prediction model when respectively supplied with the cluster quantitation vector values for each embedding cluster in addition to a set of one or more baseline features; and selecting, by the computing system, one or more embedding clusters of the number of embedding clusters for use as machine-learning features based at least in part on the respective changes in performance of the machine-learned prediction model associated with the embedding clusters.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1A:
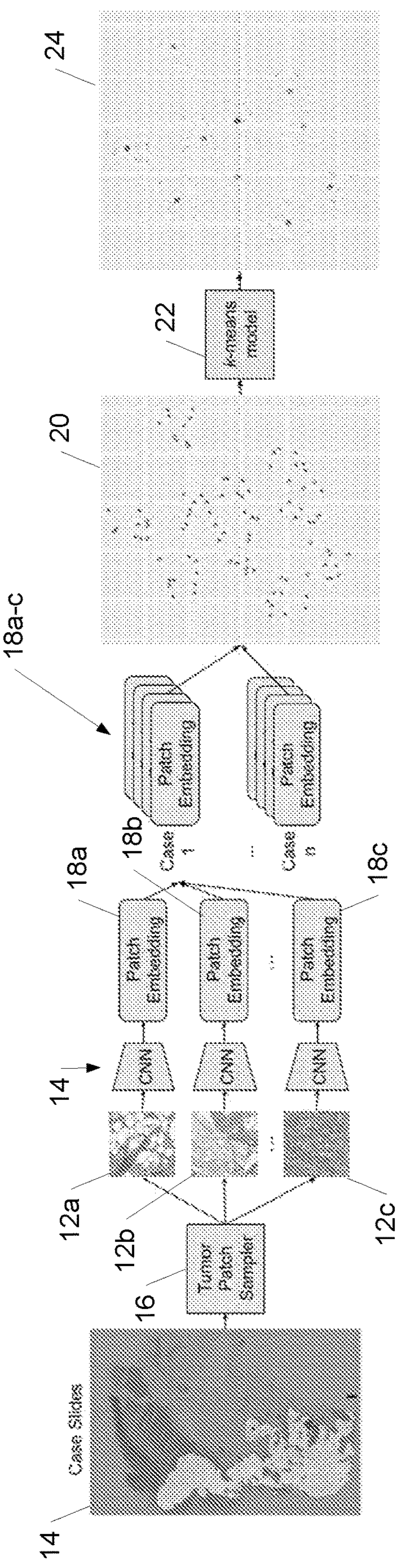
FIGS. 1A-C depict graphical diagrams of example techniques to generate, select, and use machine learning features according to example embodiments of the present disclosure.

Reference numerals that are repeated across plural figures are intended to identify the same features in various implementations.

DETAILED DESCRIPTION

Overview

Generally, the present disclosure is directed to systems and methods for the generation of machine-learning features by clustering deep learning embeddings and selecting embedding cluster data while controlling for known associations. In particular, a computing system can use a pre-trained machine learning model (e.g., an image embedding model) to obtain embeddings of input images. The computing system can train a clustering algorithm (e.g., a k-means algorithm) to cluster these embeddings into one of a number (e.g., k) clusters. The computing system can then perform a selection process to select one or more (e.g., the top n) clusters that boost performance in a prediction model (e.g., a logistic regression model) trained with a combination of the selected clusters and one or more baseline features. In such fashion, the computer system can enable an improved combination of extracted deep learned features and baseline features. This can have the effect of maximizing generalizable performance while controlling for known variables.

The systems and methods of the present disclosure provide a number of technical effects and benefits. As one example, the systems and methods of the present disclosure can provide for improved model performance on a particular task. Some example tasks can include image processing tasks such as image classification, object detection, etc. Other example tasks can include diagnostic tasks such as providing a predicted diagnosis (e.g., in the form of a probabilistic classification). One example task that spans these types of tasks is a diagnostic task in which the model generates a predicted diagnosis (e.g., prediction regarding the probability of presence of a certain disease (e.g., cancer, virulent disease, diabetes, etc.)) when provided with imagery (e.g., histological imagery, radiological imagery, natural imagery (e.g., standard imagery captured with a camera), audiographic imagery (e.g., spectrograms), and/or other forms of imagery). Thus, the performance of a computing system containing the model relative to a task (e.g., image processing) can be improved. The improvement can be in terms of accuracy and/or other performance measures such as generalizability to unseen data/domains. Thus, the present disclosure provides an improvement in the performance of a computing system itself.

As another example technical effect, the present disclosure enables the use of a prediction model with a smaller size (e.g., in terms of number of parameters, required storage space, etc.). In particular, rather than a prediction model that receives an entirety of multiple learned embeddings for a given case, the prediction model can receive a smaller set of quantitation vector values as input. By enabling the prediction model to have an input of a smaller size, the prediction model can also be made smaller (e.g., in terms of number of parameters, required storage space, etc.). This conserves computational resources such as memory usage, processor usage, network bandwidth, etc.

As another example technical effect, the proposed approaches can enable an improved combination of extracted deep learned features and baseline features. This can have the effect of maximizing generalizable performance while controlling for known variables. In particular, certain existing approaches fail to control for known feature associations. For example, certain existing approaches may use only the learned embedding or may use the entire embedding in combination with baseline features. These approaches fail to account for the issue that the embedding as a whole may encode the same known associations and, therefore, these approaches do not control for the known feature associations. However, in the approach proposed herein, the cluster generation and selection process identifies the clusters that provide information that is useful in addition to and beyond the known associations. Therefore, by extracting the quantitation values for these clusters and then combining with the baseline features, the relevant information from the embeddings can be extracted and combined with the baseline features to provide improved generalization and performance.

With reference now to the Figures, example embodiments of the present disclosure will be discussed in further detail.

Example Feature Selection Techniques

Figure 1B:
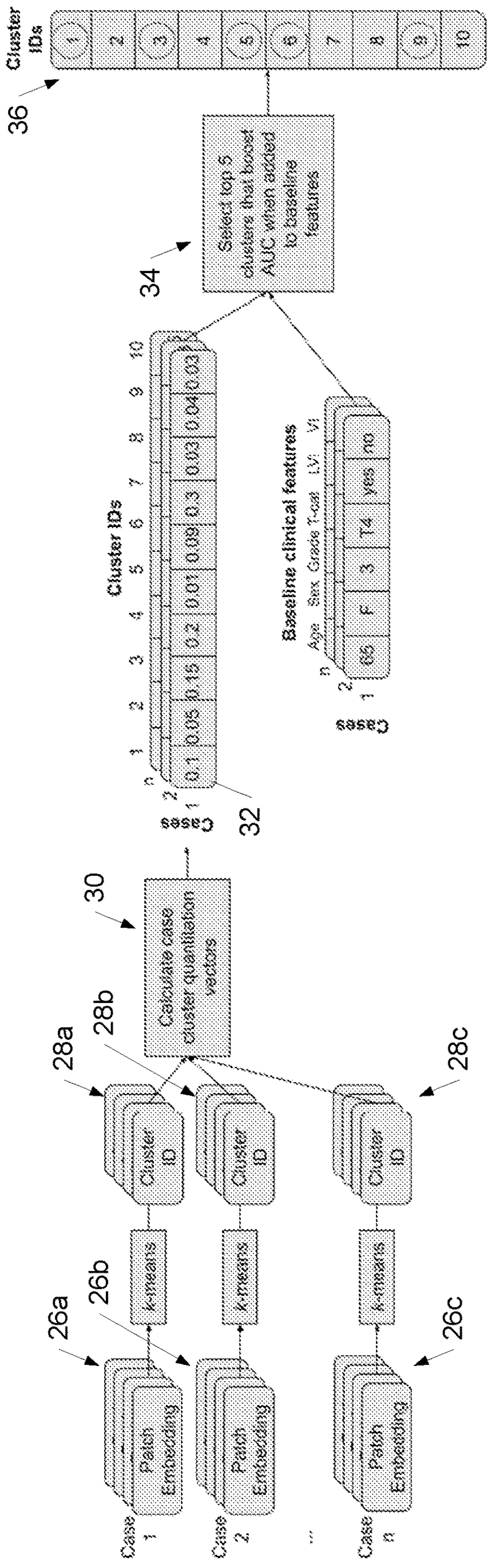
Figure 1C:
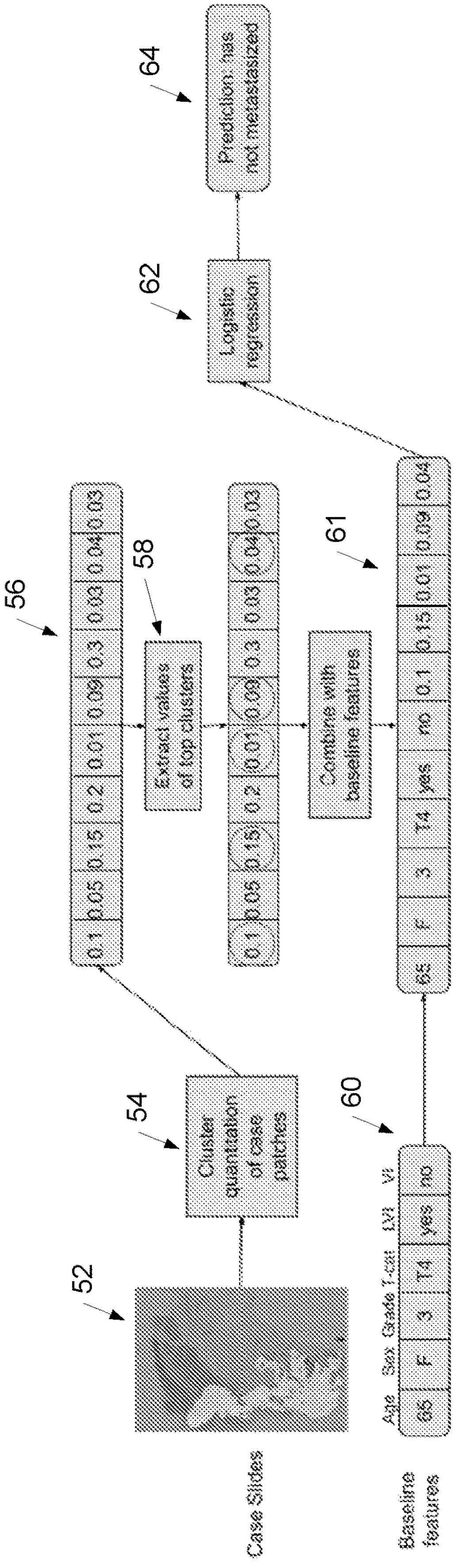

FIGS. 1A-C depict graphical diagrams of example techniques to generate, select, and use machine learning features. FIGS. 1A-C depict an example implementation of the proposed techniques as relates to the task of generating a diagnosis based on histological images. This example task is an example only. The techniques described herein can be broadly applied to many different tasks (e.g., any multi-instance learning tasks).

FIG. 1A shows an example cluster generation process. As shown in FIG. 1A, a computing system can a plurality of initial images (example initial images shown as 12*a-c*). In some implementations, the initial images 12*a-c* can be patches sampled from a larger image 14. For example, the patches 12*a-c* can be extracted from the full image 14 using a sampler 16. In some implementations, the patches can be sampled randomly. In some implementations, the sampler 16 can be or include an object detection model and the patches can be sampled based on bounding boxes output by the object detection model. In other implementations, the initial images 12*a-c* are not patches but are full images themselves.

Although FIG. 1A shows histological images, the proposed techniques are equally applicable to radiological imagery, natural imagery (e.g., standard imagery captured with a camera), audiographic imagery (e.g., spectrograms), light detection and ranging imagery, and/or other forms of imagery. More generally, the proposed approaches can be used to select specific clusters from a larger number of clusters generated from embeddings, where the embeddings were generated from other modalities of data beyond just imagery (e.g., also including embeddings generated from textual data, statistical data, sensor data, audio data, tabular data, etc.).

Referring still to FIG. 1A, the computing system can process the initial set of images 12*a-c* with a machine-learned image embedding model 14 to generate an initial set of image embeddings 18*a-c*. Embeddings 18*a-c* relate to a first case. The same process can be performed for n cases to generate a larger set of embeddings across multiple cases (e.g., as visualized at 20).

As shown in FIG. 1A, in some implementations, the machine-learned image embedding model 14 can be a neural network such as, for example, a convolutional neural network. In some implementations, the machine-learned image embedding model 14 can be a pre-trained image embedding model that has been previously trained on out-of-distribution imagery. Alternatively or additionally, machine-learned image embedding model 14 can have been pre-trained on in-distribution imagery. For example, for a task that includes analyzing histological images, the machine-learned image embedding model 14 can have been pre-trained on in-distribution imagery (i.e., histological images) and/or out-of-distribution images (e.g., natural images).

The computing system can perform a clustering algorithm 22 on the initial set of image embeddings 20 to establish a number of embedding clusters having cluster centroids (e.g., as visualized at 24). As one example, as shown in FIG. 1A, the clustering algorithm can be a k-means algorithm. However, other clustering algorithms can be used instead. In some implementations, the number of clusters k can be treated as a hyperparameter which can be manually selected and/or optimized using various hyperparameter technique (s).

Thus, in FIG. 1A, a computer system can process an initial set of images to generate image embeddings. The image embeddings can be clustered to generate a number of embedding clusters. The embedding clusters can, for example, then be fixed as held static in later portions of the technique.

FIG. 1B shows an example technique for selecting from the generated clusters (e.g., as shown in FIG. 1A) for use as machine learning features. In particular, following the cluster generation process shown in FIG. 1A, the computing system can determine which clusters provide information that is useful for supplementing baseline features for a predictive task.

More particularly, the computing system can obtain a plurality of training cases. Each training case can have a plurality of training images associated therewith (not shown in FIG. 1B). These training images may be the same, different, overlapping, or non-overlapping as the initial images discussed with reference to FIG. 1A. For example, in some implementations, FIG. 1A can be performed for a small subset of a training dataset, while FIG. 1B can be performed for the entire training dataset.

The computing system can process the plurality of images associated with each of the plurality of training cases with a machine-learned image embedding model to generate a plurality of image embeddings 26*a-c* respectively for the plurality of images. The machine-learned image embedding model can be the same as model 14 described with reference to FIG. 1A.

Referring still to FIG. 1B, the computing system can assign each image embedding to one of the number of embedding clusters (e.g., the clusters established as described with reference to FIG. 1A). This can result in each embedding 26*a-c* being assigned a cluster ID (e.g., as shown at 28*a-c*). In some implementations, the cluster assignment is an assignment of the embedding to a static cluster centroid based on distance (e.g., L1 distance, L2 distance, cosine distance) from the embedding to the centroid in the embedding space. In other implementations, the cluster centroids can be updated during the cluster assignment process shown in FIG. 1B.

As shown at 30, the computing system can generate a respective cluster quantitation vector for each training case that indicates an amount of the image embeddings associated with such training case that were assigned to each of the number of embedding clusters. For example, cluster quantitation vector 32 is shown for Case 1. Cluster quantitation vector 32 indicates that: 10% (0.1) of the embeddings 26*a* for Case 1 were assigned (e.g., at 28*a*) to cluster 1; 5% (0.05) of the embeddings 26*a* for Case 1 were assigned (e.g., at 28*a*) to cluster 1; and so forth.

As shown at 34, the computing system can evaluate a respective change in performance of a machine-learned prediction model when respectively supplied with the cluster quantitation vector values for each embedding cluster in addition to a set of one or more baseline features. The computing system can then select one or more embedding clusters of the number of embedding clusters for use as machine-learning features based at least in part on the respective changes in performance of the machine-learned prediction model associated with the embedding clusters. For example, as shown at 36, the process has resulted in selection of cluster IDs 1, 3, 5, 6, and 9.

In some implementations, at 34, the computing system can evaluate the respective change in an area under the curve performance metric for the machine-learned prediction model when respectively supplied with the cluster quantitation vector values for each embedding cluster in addition to the set of one or more baseline features. However, area under curve (AUC) is only one example performance metric that can be used. Other performance metrics (e.g., accuracy, recall, false negative rate, etc.) can be evaluated in addition or alternatively to AUC.

In some implementations, the selection process shown at 34 can be a more simplistic process in which each cluster is evaluated individually once and the best cluster(s) are then selected. In other implementations, more complex selection approaches can be used. For example, in some implementations, the computing system can iteratively select two or more of the embedding clusters in a greedy stepwise fashion. For example, this can include evaluating each cluster individually, selecting the top performing cluster, evaluating each remaining cluster in combination with the selected cluster, selecting the top performing cluster, evaluating each remaining cluster in combination with the selected clusters, and so forth until a stopping event occurs. The stopping event can include: the number of selected clusters meeting a threshold, the relative change in performance when adding another cluster dropping below a threshold, and/or other measures. In some implementations, the number of selected clusters can be treated as a hyperparameter which can be manually selected and/or optimized using various hyperparameter technique(s).

FIG. 1C shows an example process for using the selected machine learning features (e.g., as selected by the process shown in FIG. 1B).

The computing system can receive an inference case comprising a plurality of inference images. For example, the plurality of inference images can be generated from a larger inference image 52.

As shown at 54, the computing system can perform operations similar as to described with reference to FIGS. 1A and B, including: processing the plurality of inference images with a machine-learned image embedding model to generate a plurality of inference embeddings respectively for the plurality of inference images; assigning each inference embedding to one of a number of pre-defined embedding clusters; and generating an inference cluster quantitation vector 56 for the inference case that indicates an amount of the inference embeddings that were assigned to each of the number of pre-defined embedding clusters.

As shown at 58, the computing system can extract cluster quantitation vector values of the inference cluster quantitation vector 56 that correspond to one or more selected embedding clusters. With reference to FIG. 1C, the extracted cluster quantitation vector values are shown circled, and correspond, in the illustrated example, to clusters 1, 3, 5, 6, and 9 (e.g., as selected in the example shown in FIG. 1B). Although the specific values of the vector 56 match those of vector 32 of FIG. 1B, this is for illustrative purposes only, different cases will have different cluster quantitation values.

Referring still to FIG. 1B, the computing system can then combine the extracted cluster quantitation vector values of the inference cluster quantitation vector 56 and one or more baseline feature values 60 associated with the inference case to generate a combined vector 61.

The computing system can process the combined vector 61 with a machine-learned prediction model 62 to generate a prediction 64 for the inference case. In some implementations, the machine-learned prediction model comprises a logistic regression model. However, other models (e.g., various forms of neural networks, etc.) can be used additionally or alternatively. In some implementations, the machine-learned prediction model 62 can be a diagnostic model that generates a predicted medical diagnosis 64. For example, the prediction 64 can be a predicted probability of a presence of a cancerous cell within the images associated with the case. However, this is provided as an example; other tasks can be performed additionally or alternatively.

Example Devices and Systems

Figure 2A:
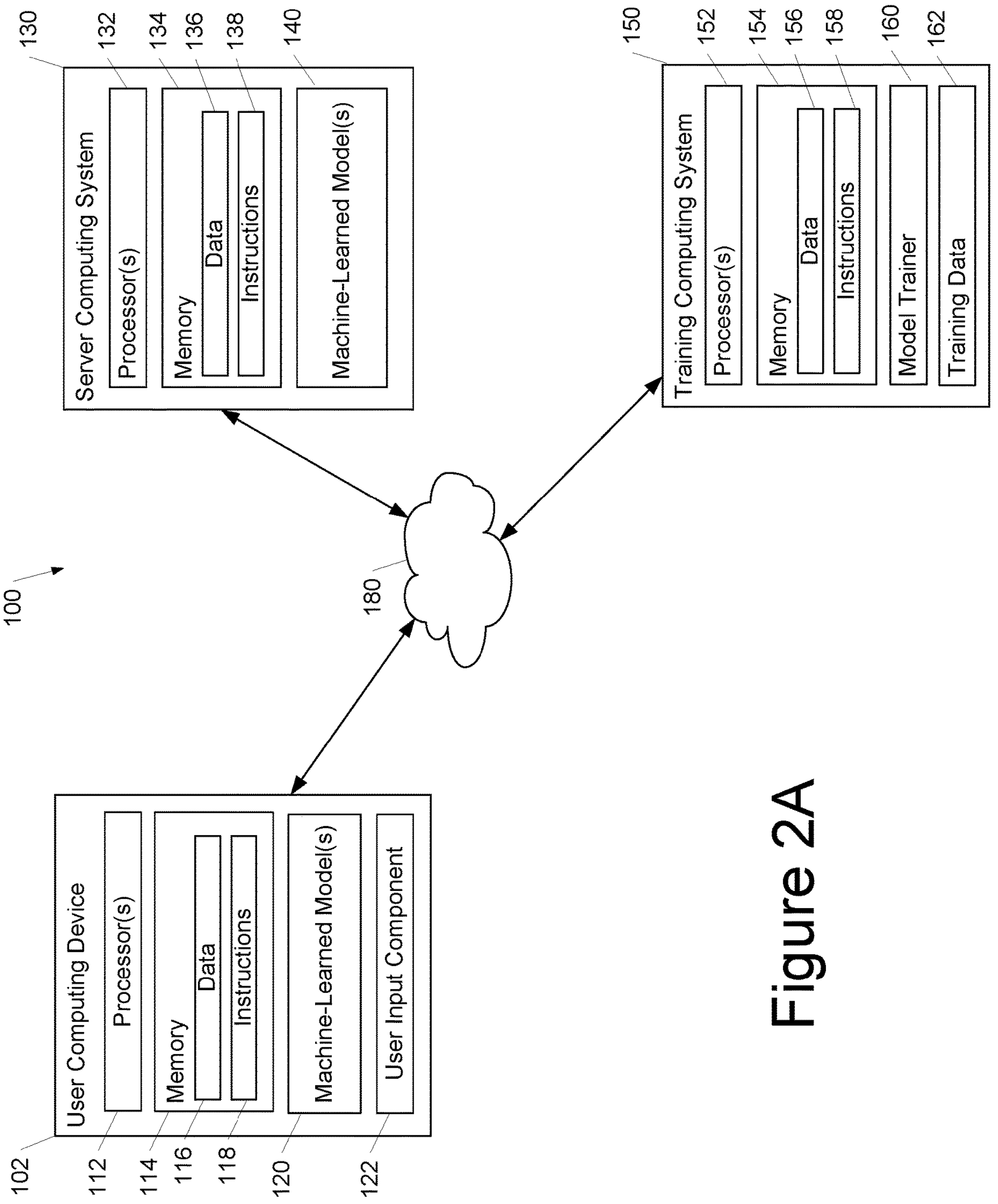
FIG. 2A depicts a block diagram of an example computing system according to example embodiments of the present disclosure.

FIG. 2A depicts a block diagram of an example computing system 100 according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more machine-learned models 120. For example, the machine-learned models 120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Some example machine-learned models can leverage an attention mechanism such as self-attention. For example, some example machine-learned models can include multi-headed self-attention models (e.g., transformer models). Example machine-learned models 120 are discussed with reference to FIGS. 1A-C.

In some implementations, the one or more machine-learned models 120 can be received from the server computing system 130 over network 180, stored in the user computing device memory 114, and then used or otherwise implemented by the one or more processors 112. In some implementations, the user computing device 102 can implement multiple parallel instances of a single machine-learned model 120 (e.g., to perform parallel prediction across multiple instances of inputs).

Additionally or alternatively, one or more machine-learned models 140 can be included in or otherwise stored and implemented by the server computing system 130 that communicates with the user computing device 102 according to a client-server relationship. For example, the machine-learned models 140 can be implemented by the server computing system 140 as a portion of a web service (e.g., a prediction service). Thus, one or more models 120 can be stored and implemented at the user computing device 102 and/or one or more models 140 can be stored and implemented at the server computing system 130.

The user computing device 102 can also include one or more user input components 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more machine-learned models 140. For example, the models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Some example machine-learned models can leverage an attention mechanism such as self-attention. For example, some example machine-learned models can include multi-headed self-attention models (e.g., transformer models). Example models 140 are discussed with reference to FIGS. 1A-C.

The user computing device 102 and/or the server computing system 130 can train the models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, an FPGA, a controller, a microcontroller, etc.) and can be one processor or a plurality of processors that are operatively connected. The memory 154 can include one or more non-transitory computer-readable storage media, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing device 102 and/or the server computing system 130 using various training or learning techniques, such as, for example, backwards propagation of errors. For example, a loss function can be backpropagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations.

In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train the machine-learned models 120 and/or 140 based on a set of training data 162. In some implementations, if the user has provided consent, the training examples can be provided by the user computing device 102. Thus, in such implementations, the model 120 provided to the user computing device 102 can be trained by the training computing system 150 on user-specific data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM, hard disk, or optical or magnetic media. The model trainer 160 can perform some or all of the operations illustrated and/or discussed with reference to FIGS. 1A-C.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

The machine-learned models described in this specification may be used in a variety of tasks, applications, and/or use cases.

In some implementations, the input to the machine-learned model(s) of the present disclosure can be image data. The machine-learned model(s) can process the image data to generate an output. As an example, the machine-learned model(s) can process the image data to generate an image recognition output (e.g., a recognition of the image data, a latent embedding of the image data, an encoded representation of the image data, a hash of the image data, etc.). As another example, the machine-learned model(s) can process the image data to generate an image segmentation output. As another example, the machine-learned model(s) can process the image data to generate an image classification output. As another example, the machine-learned model(s) can process the image data to generate an image data modification output (e.g., an alteration of the image data, etc.). As another example, the machine-learned model(s) can process the image data to generate an encoded image data output (e.g., an encoded and/or compressed representation of the image data, etc.). As another example, the machine-learned model (s) can process the image data to generate an upscaled image data output. As another example, the machine-learned model (s) can process the image data to generate a prediction output.

In some implementations, the input to the machine-learned model(s) of the present disclosure can be text or natural language data. The machine-learned model(s) can process the text or natural language data to generate an output. As an example, the machine-learned model(s) can process the natural language data to generate a language encoding output. As another example, the machine-learned model(s) can process the text or natural language data to generate a latent text embedding output. As another example, the machine-learned model(s) can process the text or natural language data to generate a translation output. As another example, the machine-learned model(s) can process the text or natural language data to generate a classification output. As another example, the machine-learned model(s) can process the text or natural language data to generate a textual segmentation output. As another example, the machine-learned model(s) can process the text or natural language data to generate a semantic intent output. As another example, the machine-learned model(s) can process the text or natural language data to generate an upscaled text or natural language output (e.g., text or natural language data that is higher quality than the input text or natural language, etc.). As another example, the machine-learned model(s) can process the text or natural language data to generate a prediction output.

In some implementations, the input to the machine-learned model(s) of the present disclosure can be speech data. The machine-learned model(s) can process the speech data to generate an output. As an example, the machine-learned model(s) can process the speech data to generate a speech recognition output. As another example, the machine-learned model(s) can process the speech data to generate a speech translation output. As another example, the machine-learned model(s) can process the speech data to generate a latent embedding output. As another example, the machine-learned model(s) can process the speech data to generate an encoded speech output (e.g., an encoded and/or compressed representation of the speech data, etc.). As another example, the machine-learned model(s) can process the speech data to generate an upscaled speech output (e.g., speech data that is higher quality than the input speech data, etc.). As another example, the machine-learned model(s) can process the speech data to generate a textual representation output (e.g., a textual representation of the input speech data, etc.). As another example, the machine-learned model(s) can process the speech data to generate a prediction output.

In some implementations, the input to the machine-learned model(s) of the present disclosure can be latent encoding data (e.g., a latent space representation of an input, etc.). The machine-learned model(s) can process the latent encoding data to generate an output. As an example, the machine-learned model(s) can process the latent encoding data to generate a recognition output. As another example, the machine-learned model(s) can process the latent encoding data to generate a reconstruction output. As another example, the machine-learned model(s) can process the latent encoding data to generate a search output. As another example, the machine-learned model(s) can process the latent encoding data to generate a reclustering output. As another example, the machine-learned model(s) can process the latent encoding data to generate a prediction output.

In some implementations, the input to the machine-learned model(s) of the present disclosure can be statistical data. Statistical data can be, represent, or otherwise include data computed and/or calculated from some other data source. The machine-learned model(s) can process the statistical data to generate an output. As an example, the machine-learned model(s) can process the statistical data to generate a recognition output. As another example, the machine-learned model(s) can process the statistical data to generate a prediction output. As another example, the machine-learned model(s) can process the statistical data to generate a classification output. As another example, the machine-learned model(s) can process the statistical data to generate a segmentation output. As another example, the machine-learned model(s) can process the statistical data to generate a visualization output. As another example, the machine-learned model(s) can process the statistical data to generate a diagnostic output.

In some implementations, the input to the machine-learned model(s) of the present disclosure can be sensor data. The machine-learned model(s) can process the sensor data to generate an output. As an example, the machine-learned model(s) can process the sensor data to generate a recognition output. As another example, the machine-learned model(s) can process the sensor data to generate a prediction output. As another example, the machine-learned model(s) can process the sensor data to generate a classification output. As another example, the machine-learned model(s) can process the sensor data to generate a segmentation output. As another example, the machine-learned model(s) can process the sensor data to generate a visualization output. As another example, the machine-learned model(s) can process the sensor data to generate a diagnostic output. As another example, the machine-learned model(s) can process the sensor data to generate a detection output.

In some cases, the machine-learned model(s) can be configured to perform a task that includes encoding input data for reliable and/or efficient transmission or storage (and/or corresponding decoding). For example, the task may be an audio compression task. The input may include audio data and the output may comprise compressed audio data. In another example, the input includes visual data (e.g. one or more images or videos), the output comprises compressed visual data, and the task is a visual data compression task. In another example, the task may comprise generating an embedding for input data (e.g. input audio or visual data).

In some cases, the input includes visual data and the task is a computer vision task. In some cases, the input includes pixel data for one or more images and the task is an image processing task. For example, the image processing task can be image classification, where the output is a set of scores, each score corresponding to a different object class and representing the likelihood that the one or more images depict an object belonging to the object class. The image processing task may be object detection, where the image processing output identifies one or more regions in the one or more images and, for each region, a likelihood that region depicts an object of interest. As another example, the image processing task can be image segmentation, where the image processing output defines, for each pixel in the one or more images, a respective likelihood for each category in a predetermined set of categories. For example, the set of categories can be foreground and background. As another example, the set of categories can be object classes. As another example, the image processing task can be depth estimation, where the image processing output defines, for each pixel in the one or more images, a respective depth value. As another example, the image processing task can be motion estimation, where the network input includes multiple images, and the image processing output defines, for each pixel of one of the input images, a motion of the scene depicted at the pixel between the images in the network input.

In some cases, the input includes audio data representing a spoken utterance and the task is a speech recognition task. The output may comprise a text output which is mapped to the spoken utterance. In some cases, the task comprises encrypting or decrypting input data. In some cases, the task comprises a microprocessor performance task, such as branch prediction or memory address translation.

FIG. 2A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data.

Figure 2B:
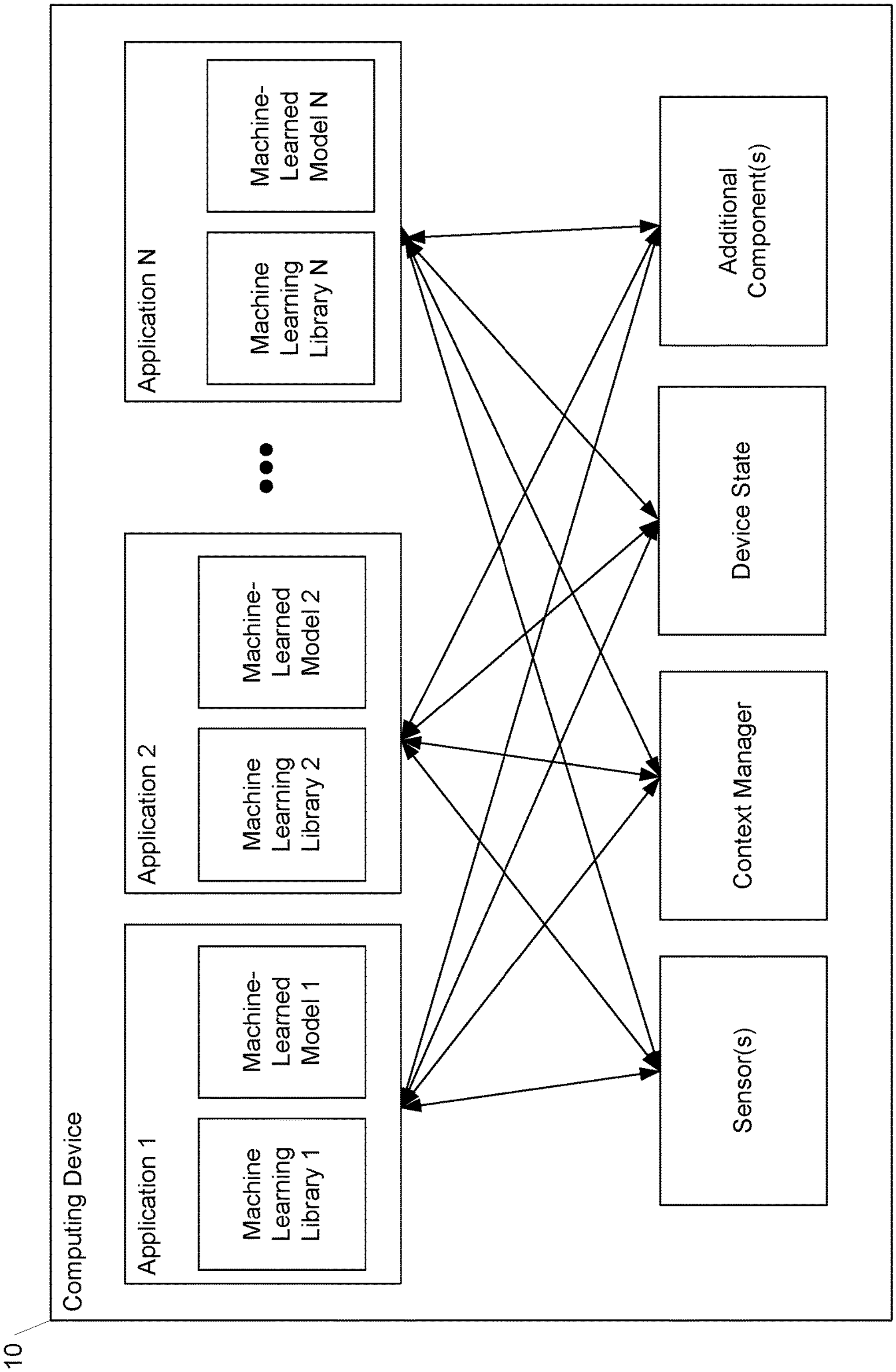
FIG. 2B depicts a block diagram of an example computing device according to example embodiments of the present disclosure.

FIG. 2B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 2B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 2C:
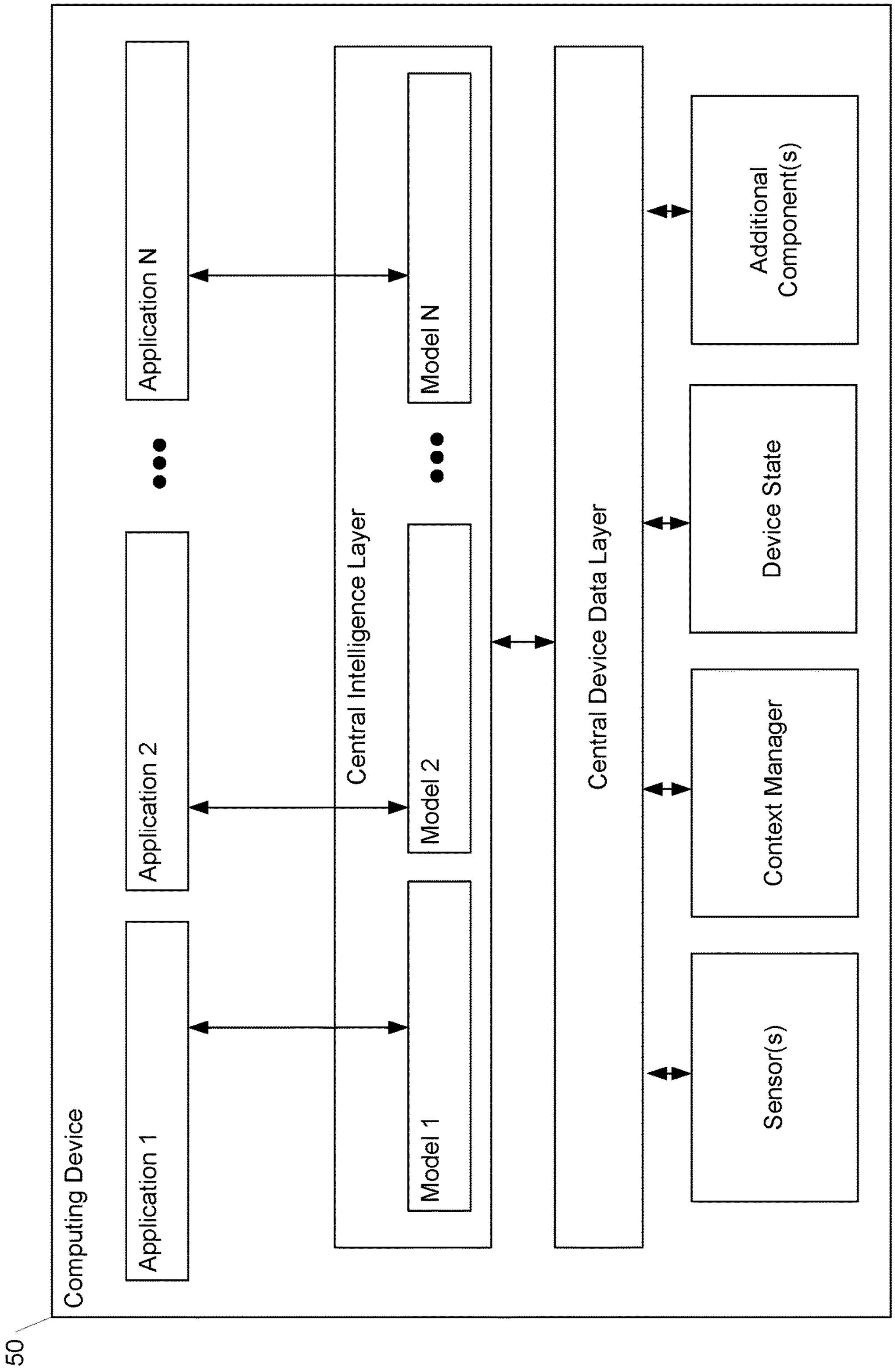
FIG. 2C depicts a block diagram of an example computing device according to example embodiments of the present disclosure.

FIG. 2C depicts a block diagram of an example computing device 50 that performs according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 2C, a respective machine-learned model can be provided for each application and managed by the central intelligence layer. In other implementations, two or more applications can share a single machine-learned model. For example, in some implementations, the central intelligence layer can provide a single model for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 2C, the central device data layer can communicate with a number of other components of the computing device, such as, for example, one or more sensors, a context manager, a device state component, and/or additional components. In some implementations, the central device data layer can communicate with each device component using an API (e.g., a private API).

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method to generate machine-learning features, the method comprising: obtaining, by a computing system comprising one or more computing devices, a plurality of training cases, wherein each training case has a plurality of training images associated therewith;

processing, by the computing system, the plurality of training images associated with each of the plurality of training cases with a machine-learned image embedding model to generate a plurality of image embeddings respectively for the plurality of training images;

assigning, by the computing system, each image embedding to one of a number of embedding clusters; generating, by the computing system, a respective cluster quantitation vector for each training case that indicates an amount of the image embeddings associated with such training case that were assigned to each of the number of embedding clusters;

evaluating, by the computing system, a respective change in performance of a machine-learned prediction model when respectively supplied with the cluster quantitation vector values for each embedding cluster in addition to a set of one or more baseline features;

and selecting, by the computing system, one or more embedding clusters of the number of embedding clusters for use as machine-learning features based at least in part on the respective changes in performance of the machine-learned prediction model associated with the embedding clusters.

2. The computer-implemented method of claim 1, wherein the plurality of training images associated with each training case comprise patches sampled from a larger image.

3. The computer-implemented method of claim 1, further comprising, prior to assigning, by the computing system, each image embedding to one of the number of embedding clusters:

processing, by the computing system, an initial set of images with the machine-learned image embedding model to generate an initial set of image embeddings; and performing, by the computing system, a clustering algorithm on the initial set of image embeddings to establish the number of embedding clusters having cluster centroids.

4. The computer-implemented method of claim 3, wherein the clustering algorithm comprises a k-means clustering algorithm.

5. The computer-implemented method of claim 1, wherein evaluating, by the computing system, the respective change in performance of the machine-learned prediction model when respectively supplied with the cluster quantitation vector values for each embedding cluster in addition to the set of one or more baseline features comprises evaluating, by the computing system, the respective change in an area under the curve performance metric for the machine-learned prediction model when respectively supplied with the cluster quantitation vector values for each embedding cluster in addition to the set of one or more baseline features.

6. The computer-implemented method of claim 1, wherein selecting, by the computing system, the one or more embedding clusters for use as machine-learning features comprises iteratively selecting, by the computing system, two or more of the embedding clusters in a greedy stepwise fashion.

7. The computer-implemented method of claim 1, wherein the machine-learned image embedding model comprises a pre-trained image embedding model that has been previously trained on out-of-distribution imagery.

8. The computer-implemented method of claim 1, wherein the machine-learned image embedding model comprises a pre-trained image embedding model that has been previously trained on in-distribution imagery.

9. The computer-implemented method of claim 1, wherein the machine-learned prediction model comprises a logistic regression model.

10. The computer-implemented method of claim 1, wherein the machine-learned prediction model comprises a diagnostic model that generates a predicted medical diagnosis.

11. The computer-implemented method of claim 10, wherein, for each training case, the medical diagnosis comprises a predicted probability of a presence of a cancerous cell within the plurality of training images associated with the training case.

12. The computer-implemented method of claim 1, wherein the plurality of training images comprise a plurality of histological images.

13. The computer-implemented method of claim 1, wherein:

the number of embedding clusters and a number of the one or more embedding clusters selected for use as machine-learning features comprise hyperparameters; and the method comprises performing a hyperparameter tuning process to determine values for the number of embedding clusters and the number of the one or more embedding clusters selected for use as machine-learning features.

14. The computer-implemented method of claim 1, further comprising:

receiving, by the computing system, an inference case comprising a plurality of inference images;

processing, by the computing system, the plurality of inference images with the machine-learned image embedding model to generate a plurality of inference embeddings respectively for the plurality of inference images;

assigning, by the computing system, each inference embedding to one of the number of embedding clusters;

generating, by the computing system, an inference cluster quantitation vector for the inference case that indicates an amount of the inference embeddings that were assigned to each of the number of embedding clusters;

extracting, by the computing system, cluster quantitation vector values of the inference cluster quantitation vector that correspond to the selected embedding clusters; and processing, by the computing system, the extracted cluster quantitation vector values of the inference cluster quantitation vector and one or more baseline feature values associated with the inference case with the machine-learned prediction model to generate a prediction for the inference case.

15. A computer system, comprising:

one or more processors; and one or more non-transitory computer-readable media that store instructions that, when executed by the one or more processors, cause the computer system to perform operations, the operations comprising:

receiving, by the computing system, an inference case comprising a plurality of inference images;

processing, by the computing system, the plurality of inference images with a machine-learned image embedding model to generate a plurality of inference embeddings respectively for the plurality of inference images;

assigning, by the computing system, each inference embedding to one of a number of pre-defined embedding clusters;

generating, by the computing system, an inference cluster quantitation vector for the inference case that indicates an amount of the inference embeddings that were assigned to each of the number of pre-defined embedding clusters;

extracting, by the computing system, cluster quantitation vector values of the inference cluster quantitation vector that correspond to one or more selected embedding clusters, the one or more selected embedding clusters having been selected based on respective changes in performance of a machine-learned prediction model when respectively supplied with cluster quantitation vector values for each embedding cluster in addition to a set of one or more baseline features; and processing, by the computing system, the extracted cluster quantitation vector values of the inference cluster quantitation vector and one or more baseline feature values associated with the inference case with the machine-learned prediction model to generate a prediction for the inference case.

16. The computer system of claim 15, wherein the plurality of inference images associated with the inference case comprise patches sampled from a larger inference image.

17. The computer system of claim 15, wherein the machine-learned image embedding model comprises a pre-trained image embedding model.

18. The computer system of claim 15, wherein the machine-learned prediction model comprises a logistic regression model.

19. The computer system of claim 15, wherein the machine-learned prediction model comprises a diagnostic model that generates a predicted medical diagnosis for the inference case.

20. The computer system of claim 15, wherein the medical diagnosis comprises a predicted probability of a presence of a cancerous cell within the plurality of inference images associated with the inference case.

* * * * *